(12) United States Patent
McGinnis et al.

(10) Patent No.: US 7,669,602 B2
(45) Date of Patent: Mar. 2, 2010

(54) SHOULDER PRESS

(76) Inventors: William J. McGinnis, 5835 Montgomery Rd., Cincinnati, OH (US) 45212; Jill C. Pickett, 932 Beacon Dr., Hobart, IN (US) 46342; Jonathan S. Citow, 565 Jackson, Glencoe, IL (US) 60025

( * ) Notice: Subject to any disclaimer, the term of this patent is extended or adjusted under 35 U.S.C. 154(b) by 103 days.

(21) Appl. No.: 11/315,060

(22) Filed: Dec. 22, 2005

(65) Prior Publication Data
US 2007/0144530 A1    Jun. 28, 2007

(51) Int. Cl.
*A61G 15/00*    (2006.01)

(52) U.S. Cl. .................................. 128/845; 378/208

(58) Field of Classification Search ............. 128/845, 128/846; 378/204, 208, 180, 195; 5/623, 5/646, 647, 601, 652, 655.7, 658
See application file for complete search history.

(56) References Cited

U.S. PATENT DOCUMENTS

| 3,707,285 | A | * | 12/1972 | Martin | 482/38 |
| 3,759,252 | A | * | 9/1973 | Berman | 602/19 |
| 3,993,088 | A | * | 11/1976 | Thomas | 135/67 |
| 4,183,520 | A | * | 1/1980 | Chase | 482/112 |
| 4,456,248 | A | * | 6/1984 | Smith | 482/142 |
| 4,616,814 | A | * | 10/1986 | Harwood-Nash et al. | 5/601 |
| 4,674,110 | A | * | 6/1987 | Eaton et al. | 378/208 |
| 5,011,216 | A | * | 4/1991 | Baughman | 296/164 |
| 5,479,471 | A | * | 12/1995 | Buckland | 378/208 |
| 6,168,548 | B1 | * | 1/2001 | Fleming | 482/23 |
| 6,820,621 | B2 | * | 11/2004 | DeMayo | 128/845 |
| 7,048,700 | B1 | * | 5/2006 | Gustie | 601/5 |

* cited by examiner

*Primary Examiner*—Patricia M Bianco
*Assistant Examiner*—Camtu T Nguyen
(74) *Attorney, Agent, or Firm*—Ariel S. Bentolila; Bay Area IP Group, LLC

(57) ABSTRACT

The invention is directed to a shoulder press for holding the shoulders of a subject out of the way of an X-ray view by exerting a downward pressure upon the shoulders by means of the device so that all the vertebrae are visible in the X-ray, the shoulder press comprising a horizontal member and two vertical members, the vertical members having attachments for placing on the shoulders of the subject.

21 Claims, 2 Drawing Sheets

SHOULDER PRESS

BACKGROUND

Field of the Invention

This invention relates generally to the field of devices and systems for neurophysiological monitoring/testing/assessment in both clinical and intraoperative settings.

During anterior cervical discectomy and fusion procedures, X-rays are may be required. The radiographic area in such a surgical procedure is constrained by anatomical obstruction by the subject's shoulders or the subject's jaw. It is rare that all seven cervical vertebral bodies are visible in a single X-ray because the jaw of the subject may obstruct the view of C1 and C2, while the shoulders of the subject may obscure C7 and the first thoracic vertebra C8.

A device that would optimize intraoperative radiography, and particularly unobstruct the radiographic area by holding the shoulders in a position so that all the vertebrae are visible in an X-ray, would be highly desirable.

SUMMARY OF THE INVENTION

A device is provided for attaching to the body of a subject for optimizing the radiographic area in a subject to be X-rayed, comprising a cross-bar; and a pair of struts, each strut being orthogonally connected at its proximal end to the cross-bar, wherein the distal end of each strut has a shoulder member for placing on a subject's shoulders, wherein the device allows for downward pressure on the subject's shoulders.

In one aspect of the invention the struts are removably connected to the cross-bar.

In a preferred embodiment, the cross-bar further comprises a pair of hand grips.

In another embodiment, the cross-bar has a first and second connector for connecting with the struts. In yet another embodiment the connectors comprise a plurality of pairs of horizontally placed apertures. In a further embodiment, the pairs of horizontally placed apertures are positioned so as to be spaced respectively approximately 10 inches, 12 inches, 14 inches, and 16 inches apart. In another embodiment, the proximal end comprises a third connector comprising for example a bolt for engaging with the horizontally placed apertures for adjusting the width between the two struts, and optionally comprising a lever for quick release of the bolt.

In another aspect of the invention, the strut comprises means for adjusting the longitudinal extension of the strut, for example where the longitudinal extension can be varied between approximately 12 inches and 30 inches.

In a preferred embodiment, each strut further comprises two portions, an upper strut portion and a lower strut portion, the upper strut portion comprising a hollow tube having a series of vertically placed apertures in the wall of the tube, the lower strut portion having a pin for engaging with the vertically placed apertures, whereby when the lower strut portion is fitted into the upper strut portion, the pin engages with one of the apertures to hold the strut in a fixed longitudinal extension. In another embodiment, the apertures are spaced such that the strut may be held in a longitudinal extension of between approximately 20 inches, 22 inches, and 24 inches. In a further embodiment, the pin comprises a push-down mechanism to disengage the pin from the aperture to adjust the longitudinal extension.

In yet another aspect of the invention, the shoulder member comprises a U-shaped grip orientated perpendicular to the plane of the horizontal member. In one embodiment, the grip comprises two portions in an adjustable conformation, each portion comprising an outer section and an inner section, the inner section being the section that is adjacent to the subject's shoulder. In a further embodiment, the grip further comprises a spring means for extending or contracting the arc of the grip allowing adjustment of the two portions to fit the subject's shoulder. In a preferred embodiment the outer section is made of clear plastic. In a further embodiment the inner section comprises a substance selected from the group consisting of foam, cotton, leather, sheep skin, silicon, a polymer, and a gel. In yet another embodiment, the inner section comprises a gel pad. In a further embodiment the spring means is made of a clear plastic.

In a preferred embodiment, the struts are made of a clear plastic. In another embodiment, the pin is made of clear plastic. In a further embodiment the cross-bar member is made of clear plastic. In yet another embodiment, the bolt is made of clear plastic.

In yet another aspect of the invention, a kit comprising a device for attaching to the body of a subject for optimizing the radiographic area in a subject to be X-rayed, comprising a cross-bar; and a pair of struts, each strut being orthogonally connected at its proximal end to the cross-bar, wherein the distal end of each strut has a shoulder member for placing on a subject's shoulders, wherein the device allows for downward pressure on the subject's shoulders, wherein the struts are removably connected to the cross-bar.

DETAILED DESCRIPTION

Figure 1A:
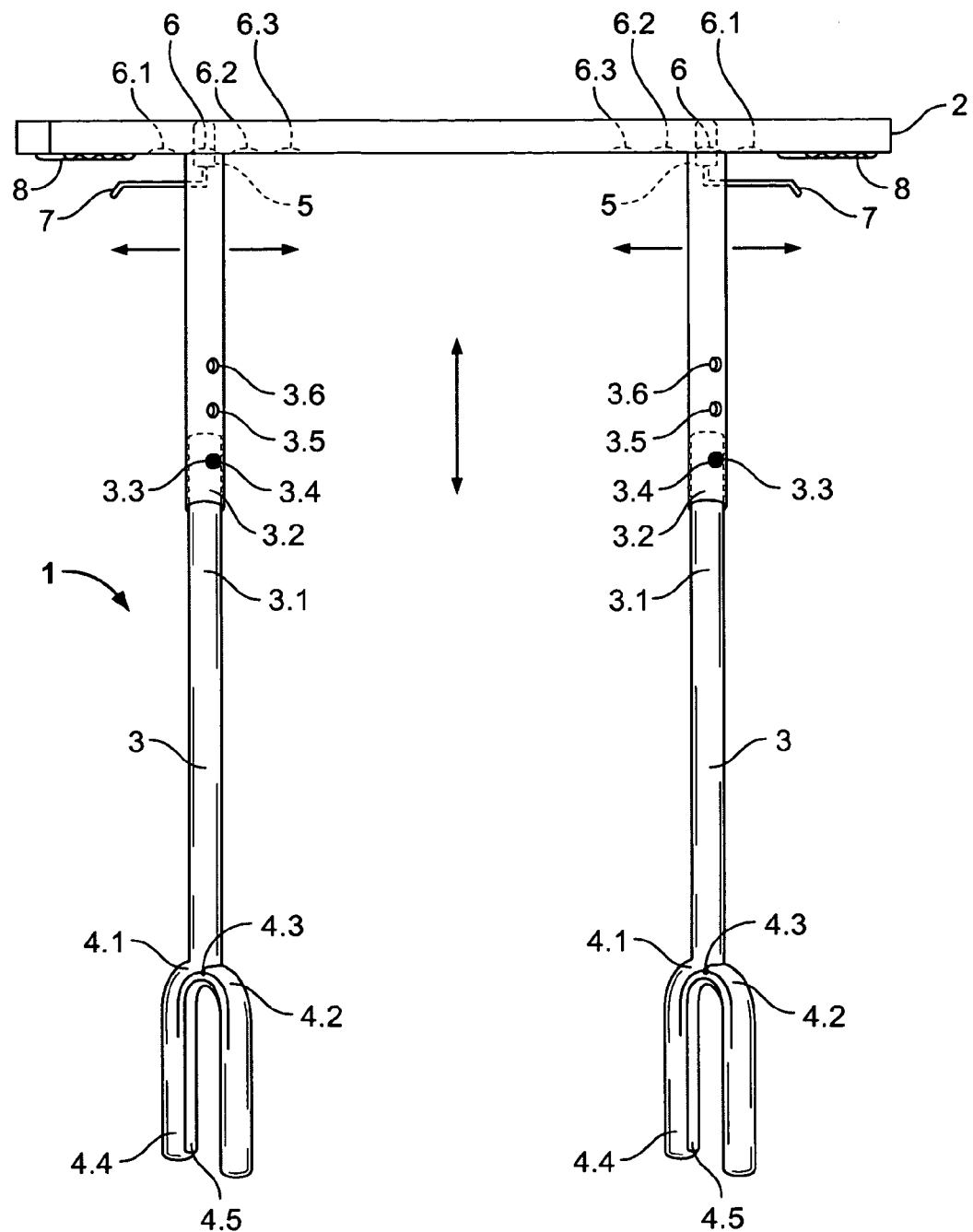
FIG. 1 is a view of one construction of the shoulder press.

Anterior and lateral x-ray views of the cervical spine are often obscured by the anatomical position of the subject's shoulders. It is of critical concern that the physician be able to correctly evaluate each segment of the cervical spine, in intraoperative and trauma situations. During X-rays of the cervical area or cervical thoracic junction, it is rare that all seven cervical vertebral bodies are visible in a single X-ray because the view of cervical vertebrae C1 and C2 may be obstructed by the jaw of the subject, and the cervical vertebra C7, and the first thoracic vertebra may be obscured by the subject's shoulders. Our intraoperative experience has led to the development of a bilateral shoulder pusher that has allowed us to push the subjects shoulder caudally to allow a more inclusive view of the anterior and lateral cervical spine films. We routinely use the shoulder pusher for correct level confirmation, following interbody device placement, proper plate placement and for post procedure confirmation.

The device provided is a shoulder press for use during the X-raying of a subject in the cervical or cervical thoracic junction regions, for holding the shoulders of a subject out of the way of an X-ray view. The device is suitable for use in the clinical and ER settings as well as for intraoperative use such as anterior cervical discectomy or fusion procedures.

The device comprises a horizontal member (or cross-bar), connected orthogonally to two vertical struts (or arms) having attached at their distal ends shoulder-attaching members, or shoulder grips, for placing on the shoulders of a subject undergoing a procedure requiring an X-ray, such as for example an anterior cervical discectomy or fusion procedure, but also a clinical setting or preoperative X-ray. The horizontal member allows for bilateral pressure to be applied to the shoulders of the subject, and when downward pressure is applied to the horizontal member, the subject's shoulders are pushed down out of the way of the X-ray view. With such a device, both C1 and C2, and C7 and C8, are visible in a single X-ray.

It will be understood by those skilled in the art that the device components may be an integral structure, being die-cast.

Or, in a preferred embodiment, the struts are removably connected to the cross-bar, so that the removable components can be disassembled for carrying. A kit contemplating such an embodiment is also provided.

In a preferred embodiment, the horizontal member has hand grips for easily exerting downward pressure on the struts.

In another preferred embodiment, the horizontal member is adjustable to allow the distance between the struts to be widened or lessened so as to be positioned shoulder width apart to suit the anatomical position of the shoulders of the subject. In another embodiment, the connecting means connecting a strut and the horizontal member further comprises a notching means so that a notch on the strut end can be slotted into a grove in the horizontal member such that the strut is positioned and locked in place.

In another preferred embodiment, the vertical struts comprise extension adjusting means for longitudinally adjusting the struts to be long enough for the horizontal member to be beyond the subject's head, so that the struts may be shortened or lengthened to suit the subject's size and the requirements of the procedural field and its requirements.

In yet another embodiment the vertical struts have a pin knob and hole means for locking the longitudinally extension in place so that the struts may be individually adjusted to better fit the patient's body frame. In such an embodiment, the strut comprises two portions, an upper strut portion and a lower portion, wherein at least the lower section of the upper portion and the upper section of the lower portion are hollow such that the lower portion can slide into and fit the upper portion, the upper portion of the strut having a series of vertically placed holes in its lower section, the lower portion of the strut having a pin knob positioned on its upper section such that when lower portion is slid into the upper portion strut, the pin knob can be slotted into one of the holes depending upon the longitudinal requirements of the strut. In a further embodiment, the strut upper and lower structure comprises a push-down mechanism for quick release.

In one embodiment, the grips and struts are made of clear plastic for X-ray transparency. In another embodiment, the inner area on the shoulder grips for contact with the subject's shoulders is encircled in a gel pad to compensate for pressure applied by the downward force on the horizontal member.

In a further embodiment, the shoulder grips further comprise an adjustment means for allowing for the anatomical variations of different subjects. In yet a further embodiment, the adjustment means is in the form of a spring allowing adjustment to the size and shape of the shoulders of the subject.

EXAMPLE

In 58 operative procedures on the anterior cervical spine the shoulder pusher device aided in all lateral and anterior c-spine films in providing a more inclusive view. One hundred and fifty four films (123 lateral, 31 anterior) were taken in all (four procedures for C3, C4 discectomy and fusion, five for C3, C4 and C4, C5, seven for C4, C5, eleven for C5, C6, nine for C4, C5 and C5, C6, one for C3, C4-C4, C5-C5, C6, nine for C6, C7, eight for C5, C6 and C6, C7, one for C7, T1 and three for C6, C7 and C7, T1.

Figure 1B:
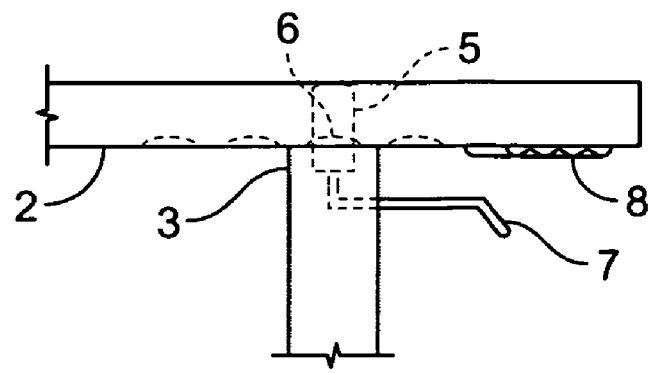

A preferred embodiment of the device is illustrated in FIGS. 1A and 1B.

FIG. 1A shows one embodiment of device 1 for optimizing the radiographic area in a subject to be X-rayed, comprising horizontal (cross-bar) member, 2, to which is connected a pair of vertical struts, 3, each strut having attached to its distal end a shoulder member for attaching to a subject's shoulders, and a proximal strut end comprising strut bolt 5 for slotting into aperture 6 on horizontal member 2. In this example, the thickness of the cross bar is ¾ inch (1.9 cm). FIG. 1B shows an enlargement of strut 3 connected to horizontal member 2, in which bolt 5 is engaged in horizontal member aperture 6. It will be understood by those skilled in the art that there are many options for providing a means for variably and/or removably attaching the vertical struts to the horizontal cross-bar member. In the embodiment shown in FIG. 1A, there are shown four apertures on either end of the horizontal member for receiving strut bolt 5, so that the width between the two struts, when connected to the horizontal member, may be adjusted to accommodate the different anatomical proportions of a subject's shoulders. Slot 6 is positioned on either end of the horizontal member so that the width between the struts when connected is approximately 14 inches apart. Slot 6.1 is positioned so that the distance between the struts is 16 inches. In similar fashion, slot 6.2 provides a width between the two connected struts of approximately 12 inches, and slot 6.3, a width of approximately 10 inches. Connected to bolt 5 is release lever 7. Hand-grip 8 provides for pressure to be applied when using the device.

In this embodiment, the struts comprise lower strut portion, 3.1 and upper strut tubular portion, 3.2, wherein the lower strut portion is fitted into the upper strut portion in one of several alternative positions provided by a pin and aperture vertical adjustment means. In this example, the thickness of the upper portion of the strut is ¾ inch (1.9 cm) and the lower portion of the strut is ⅝ inch (1.5 cm). Pin 3.3 is a depressible pin attached to lower strut portion 3.1. Upper strut portion 3.2 has several vertically spaced apertures in the tubular wall of 3.2, whereby pin 3.3 can be slotted into one of the apertures for variably extending the length of the strut. In the embodiment shown in FIG. 1A, three apertures, respectively 3.4, 3.5 and 3.6, are positioned to provide a longitudinal strut extension of, respectively, approximately 24 inches, 22 inches and 20 inches, when pin 3.3 is slotted into the respective aperture, thereby providing for adjusting the longitudinal extension of the device according to the requirements of the practitioner. In the exemplary vertical extension position of the strut shown in FIG. 1A, pin 3.3 is slotted into aperture 3.4, providing a longitudinal extension of the strut of 24 inches.

The shoulder member attached to the distal end of the strut is comprised of two sections, 4.1 and 4.2, the two sections connected via spring means 4.3 providing for the arc of the shoulder member to be extended width-wise to accommodate particular anatomical variations. The shoulder sections comprise outer portion 4.4, made of clear plastic, and inner portion 4.5, comprising a gel pad.

Figure 2:
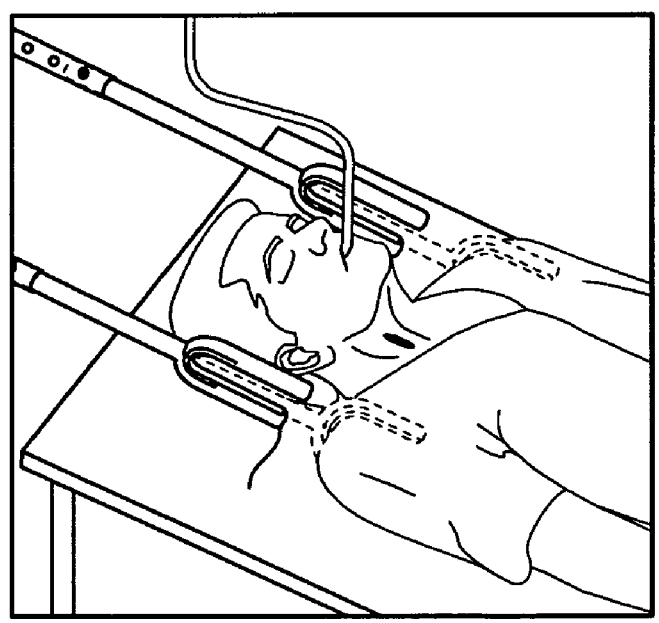
FIG. 2 illustrates an embodiment of the shoulder press in position on a subject's shoulders.

An illustration of the use of the embodiment of the device of FIG. 1, is given in FIG. 2 in which an anaesthetized subject lies on the operating table, 9 representing the surgical field, in which the subject's shoulders are pushed down by means of the device and out of the way of the X-ray field.

What is claimed is:

1. A hand-held device for optimizing the cervical vertebral radiographic area in a subject to be X-rayed, the device comprising:
   a cross-bar;
   a first strut extending orthogonally from the cross-bar, the first strut including a first end and a second end, the first end of the first strut being moveably connected to the cross-bar, and a substantially U-shaped member connected to the second end of the first strut, the U-shaped member being sized to fit on a subject's shoulder, wherein the U-shaped member comprises two portions in an adjustable conformation, each portion comprising an outer section and an inner section, the inner section being the section that is adjacent to the subject's shoulder, and a spring means for extending or contracting an arc of the U-shaped member allowing adjustment of the two portions to fit the subject's shoulder; and
   a second strut extending orthogonally from the cross-bar, the second strut including a first end and a second end, the first end of the second strut being moveably connected to the cross-bar, and a substantially U-shaped second member connected to the second end of the second strut, the U-shaped second member being sized to fit on the subject's other shoulder, wherein the U-shaped second member comprises two portions in an adjustable conformation, each portion comprising an outer section and an inner section, the inner section being the section that is adjacent to the subject's shoulder, and a spring means for extending or contracting an arc of the U-shaped second member allowing adjustment of the two portions to fit the subject's shoulder, wherein a distance between the first strut and the second strut is adjustable with movement of one of the first strut and the second strut with respect to the other of the first strut and the second strut, and wherein the U-shaped members move the subject's shoulders out of view of the cervical vertebrae when imaging the cervical vertebrae of the subject when downward pressure is applied to the cross-bar.

2. The device of claim 1, wherein the cross-bar, the first strut, the U-shaped member, the second strut and the U-shaped second member are configurable as a kit for ease of transportation.

3. The device of claim 1, wherein the cross-bar further comprises a pair of hand grips.

4. The device of claim 1, wherein the cross-bar has a first and second connector for connecting with the struts.

5. The device of claim 4, wherein the cross bar connectors comprise a plurality of apertures.

6. The device of claim 5, wherein the apertures are paired such that the paired apertures are spaced respectively at approximately 10 inches, 12 inches, 14 inches, and 16 inches apart.

7. The device of claim 4, wherein the first end of each of the struts comprises a third connector.

8. The device of claim 7, wherein the third connector is made of clear plastic.

9. The device of claim 7, further comprising a lever for releasing the third connector.

10. The device of claim 1, wherein the first strut further comprises means for adjusting the longitudinal extension of the first strut.

11. The device of claim 10, wherein the longitudinal extension can be varied between approximately 12 inches and 30 inches.

12. The device of claim 1, wherein each strut further comprises an upper strut portion and a lower strut portion, the upper strut portion comprising a hollow tube having a series of vertically placed apertures in the wall of the tube, the lower strut portion having a pin for engaging with the vertically placed apertures, whereby when the lower strut portion is fitted into the upper strut portion, the pin engages with one of the apertures to hold the struts in a fixed extension with respect to each other.

13. The device of claim 12, wherein the apertures are spaced such that the strut may be held in a longitudinal extension of between approximately 20 inches, 22 inches, and 24 inches.

14. The device of claim 12, wherein the pin further comprises a push-down mechanism to disengage the pin from the aperture to adjust the longitudinal extension.

15. The device of claim 12, wherein the pin is made of clear plastic.

16. The device of claim 1, wherein the struts are made of a clear plastic.

17. The device of claim 1, wherein the cross-bar member is made of clear plastic.

18. The device of claim 1, wherein the outer section is made of clear plastic.

19. The device of claim 1, wherein the inner section comprises a substance selected from the group consisting of foam, cotton, leather, sheep skin, silicon, a polymer, and a gel.

20. The device of claim 1, wherein the inner section comprises a gel pad.

21. The device of claim 1, wherein the spring means is made of a clear plastic.

* * * * *